(12) United States Patent
Thornes et al.

(10) Patent No.: US 9,005,245 B2
(45) Date of Patent: *Apr. 14, 2015

(54) ACROMIOCLAVICULAR JOINT FIXATION TECHNIQUE

(75) Inventors: Brian Thornes, Dublin (IE); Duncan Tennent, Banstead (GB)

(73) Assignee: Arthrex, Inc., Naples, FL (US)

( * ) Notice: Subject to any disclaimer, the term of this patent is extended or adjusted under 35 U.S.C. 154(b) by 1226 days.

This patent is subject to a terminal disclaimer.

(21) Appl. No.: 11/687,882

(22) Filed: Mar. 19, 2007

(65) Prior Publication Data

US 2007/0179531 A1    Aug. 2, 2007

Related U.S. Application Data

(63) Continuation-in-part of application No. 11/482,038, filed on Jul. 7, 2006, now Pat. No. 8,512,376, and a continuation-in-part of application No. 10/233,122, filed on Aug. 30, 2002, now Pat. No. 7,235,091.

(60) Provisional application No. 60/697,125, filed on Jul. 7, 2005, provisional application No. 60/783,869, filed on Mar. 21, 2006.

(51) Int. Cl.
*A61B 17/04* (2006.01)
*A61B 17/68* (2006.01)
*A61B 17/17* (2006.01)
*A61B 17/56* (2006.01)

(52) U.S. Cl.
CPC ............ *A61B 17/0401* (2013.01); *A61B 17/68* (2013.01); *A61B 17/0469* (2013.01); *A61B 17/1714* (2013.01); *A61B 2017/0404* (2013.01); *A61B 2017/564* (2013.01); *A61B 2017/1778* (2013.01)

(58) Field of Classification Search
CPC ............... A61B 2017/0404; A61B 2017/0414; A61B 17/0401; A61B 2002/0888; A61B 2/0811; A61B 2/0817
USPC ........... 606/232, 70, 328, 300, 282–284, 286, 606/324, 151, 74, 60, 280, 71; 623/13.11–13.14
See application file for complete search history.

(56) References Cited

U.S. PATENT DOCUMENTS

| 261,501 | A | * | 7/1882 | Vandermark et al. ....... 24/115 R |
| 4,988,351 | A | | 1/1991 | Paulos et al. |
| 5,219,359 | A | | 6/1993 | McQuilkin et al. |
| 5,306,290 | A | | 4/1994 | Martins et al. |

(Continued)

OTHER PUBLICATIONS

E.P. Su et al., "Using Suture Anchors for Coracoclavicular Fixation in Treatment of Complete Acromioclavicular Separation," May 2004, *The American Journal of Orthopedics*, pp. 256-257; Orthopaedic Surgery, Hospital for Special Surgery; New York, New York.

*Primary Examiner* — Gregory Anderson
*Assistant Examiner* — Christopher L Templeton
(74) *Attorney, Agent, or Firm* — Dickstein Shapiro LLP

(57) ABSTRACT

A reconstruction system and method for fixation of bone to bone, or soft tissue to bone. The reconstruction system comprises two fixation devices (for example, two buttons) joined by a continuous loop of flexible material. Each button is provided with at least one opening that allows the passage of the flexible material. The button may be formed, for example, of metal, PEEK or PLLA. The flexible material may be FIBERWIRE® suture.

13 Claims, 6 Drawing Sheets

(56) References Cited

U.S. PATENT DOCUMENTS

| | | | |
|---|---|---|---|
| 5,366,480 A | 11/1994 | Corriveau et al. | |
| 5,409,490 A | 4/1995 | Ethridge | |
| 5,464,426 A | 11/1995 | Bonutti | |
| 5,593,424 A | 1/1997 | Northrup, III | |
| 5,921,986 A | 7/1999 | Bonutti | |
| 5,989,256 A | 11/1999 | Kuslich et al. | |
| 6,066,160 A * | 5/2000 | Colvin et al. | 606/232 |
| 6,110,207 A * | 8/2000 | Eichhorn et al. | 623/13.14 |
| 6,494,888 B1 * | 12/2002 | Laufer et al. | 606/153 |
| 6,517,578 B2 * | 2/2003 | Hein | 623/13.13 |
| 6,533,802 B2 * | 3/2003 | Bojarski et al. | 606/232 |
| 6,635,073 B2 | 10/2003 | Bonutti | |
| 6,716,234 B2 | 4/2004 | Grafton et al. | |
| 7,153,312 B1 * | 12/2006 | Torrie et al. | 606/144 |
| 7,235,091 B2 * | 6/2007 | Thornes | 606/232 |
| 2002/0156475 A1 * | 10/2002 | Lerch et al. | 606/70 |
| 2003/0130694 A1 | 7/2003 | Bojarski et al. | |
| 2003/0236555 A1 * | 12/2003 | Thornes | 606/232 |
| 2004/0097939 A1 * | 5/2004 | Bonutti | 606/69 |
| 2004/0133238 A1 * | 7/2004 | Cerier | 606/232 |
| 2004/0199166 A1 * | 10/2004 | Schmieding et al. | 606/79 |
| 2004/0236373 A1 | 11/2004 | Anspach, III | |
| 2005/0049599 A1 * | 3/2005 | Nesper et al. | 606/72 |
| 2007/0016208 A1 | 1/2007 | Thornes | |

* cited by examiner

ACROMIOCLAVICULAR JOINT FIXATION TECHNIQUE

CROSS-REFERENCE TO RELATED APPLICATIONS

This application is a continuation-in-part of U.S. application Ser. No. 11/482,038, filed Jul. 7, 2006 now U.S. Pat. No. 8,512,376, which claims the benefit of U.S. Provisional Application No. 60/697,125, filed Jul. 7, 2005. This application also claims the benefit of U.S. Provisional Application No. 60/783,869, filed Mar. 21, 2006. The entire disclosures of these prior applications are incorporated by reference herein. This application is also a continuation-in-part of application Ser. No. 10/233,122 filed Aug. 30, 2002, now U.S. Pat. No. 7,235,091, which in turn claims priority under 35 U.S.C. §119 to IE S2002/0504 filed Jun. 20, 2002. U.S. application Ser. No. 11/482,038, filed Jul. 7, 2006, is also a continuation-in-part of application Ser. No. 10/233,122 filed Aug. 30, 2002, now U.S. Pat. No. 7,235,091, which in turn claims priority under 35 U.S.C. §119 to IE S2002/0504 filed Jun. 20, 2002.

FIELD OF THE INVENTION

The present invention relates to the field of surgery and, in particular, to a joint or ligament reconstruction technique and associated fixation and reconstruction device.

BACKGROUND OF THE INVENTION

Disruption of ligaments, such as the coracoclavicular ligament, is a common occurrence. In many cases, the injury can be treated conservatively and the only residual problem is that of a mild cosmetic deformity. Several groups of patients, however, do not tolerate the injury well. If the joint is reduced acutely and held reduced during the hearing phase, the native ligaments will heal restoring the stability of the joint.

BRIEF SUMMARY OF THE INVENTION

The present invention provides a technique and reconstruction system for fixation of bone to bone, or soft tissue to bone. The reconstruction system of the present invention comprises two fixation devices (for example, two buttons) joined by a continuous loop of flexible material. Each button is provided with at least one opening that allows the passage of the flexible material. The button may be formed, for example, of metal, PEEK or PLLA. The flexible material may be suture such as FIBERWIRE® suture, sold by Arthrex, Inc. of Naples, Fla.

The present invention also provides a method of fixation of bone to bone, or soft tissue to bone. The method of the present invention comprises the steps of: (i) providing a tunnel through a first bone and a second bone; (ii) providing a two button/suture loop construct including two buttons joined by a continuous loop of flexible material in the vicinity of the bones; (iii) advancing one of the two buttons through the first and second bones, until it exits the second bone; and (iv) advancing the other button to the surface of the first bone.

These and other features and advantages of the invention will be more apparent from the following detailed description that is provided in connection with the accompanying drawings and illustrated exemplary embodiments of the invention.

DETAILED DESCRIPTION OF THE INVENTION

Figure 1:
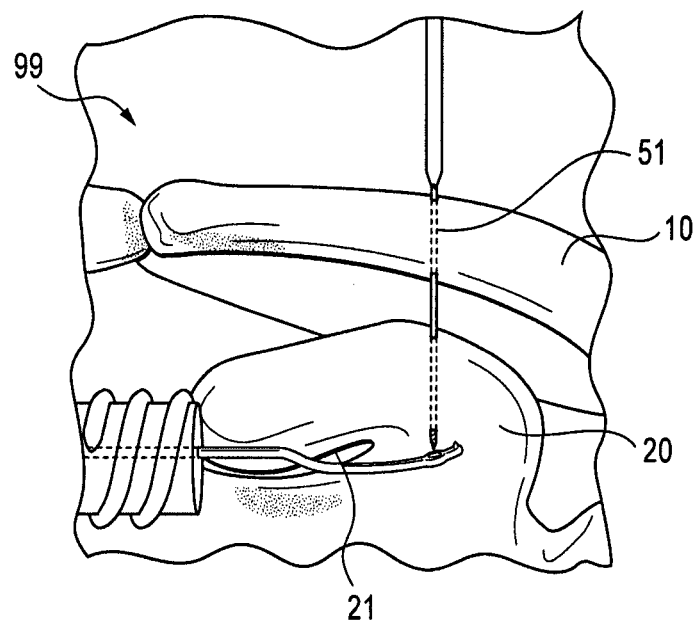
FIGS. 1-7 illustrate subsequent steps of a method of joint reconstruction in accordance with an exemplary embodiment of the present invention.

The present invention provides a technique and reconstruction system for fixation of bone to bone, or soft tissue to bone. The reconstruction system (TightRope system) of the present invention comprises two fixation devices (for example, two buttons) having various geometries (for example, circular or oblong) and being joined by a continuous loop of suture. Each button is provided with at least one opening (preferably two openings) that allow the passage of suture. The button may be formed, for example, of metal, PEEK or PLLA. The suture may be FIBERWIRE® suture, sold by Arthrex, Inc. of Naples, Fla.

The present invention also provides a method for fixation of bone to bone, or soft tissue to bone. The method of the present invention comprises the steps of: (i) providing a first hole through a first bone and a second hole through a second bone of a joint; (ii) providing a two button/suture loop construct (TightRope) including two buttons joined by a continuous loop of flexible material in the vicinity of the joint; (iii) advancing one of the two buttons through the holes in the first and second bones, until it exits the second bone; and (iv) advancing the other button to the surface of the first bone.

According to an exemplary embodiment, the present invention provides a method of acromioclavicular (AC) joint reconstruction, comprising the steps of: (i) providing a hole through the clavicle and the coracoid; (ii) providing a two button/suture loop construct (including two buttons joined by a continuous loop of suture) in the vicinity of the AC joint; (iii) advancing one of the two buttons through the hole in the clavicle and the coracoid until it exits the coracoid base; and (iv) advancing the other button to the surface of the clavicle.

According to another exemplary embodiment, and as described in more detail below, the acromioclavicular (AC) joint reconstruction technique of the present invention comprises the steps of: (i) drilling a hole of about 4 mm through the clavicle and the coracoid by using a C-Ring adapteur guide and a cannulated drill; (ii) leaving the cannulated drill in the clavicle and the coracoid; (iii) advancing a suture passing wire through the cannulated drill and subsequently removing the drill; (iv) inserting two traction sutures from the oblong button of the fixation system of the invention through the wire loop of the suture passing wire; (v) pulling the suture passing wire to retrieve the two traction sutures out of the anterior/inferior cannula; (vi) advancing the oblong button through the clavicle and the coracoid until it exits the coracoid base, and pulling on each of the traction sutures of the oblong button to flip the button onto the underside of the coracoid base, to secure the oblong button; (vii) pulling on suture tails of the round button, to advance the round button down to the surface of the clavicle; and (viii) tying the sutures to stabilize the acromioclavicular joint.

The method of the present invention has applications to joint and ligament reconstruction. Particular applications relate to acromioclavicular joint reconstructions, where the method of the present invention provides a simple, reproducible, minimally invasive technique for acute acromioclavicular joint stabilization which enables a rapid return to activity for the acute injury. The technique is indicated for acute acromioclavicular joint dislocation (Rockwood type III to VI) of less than one month duration.

Referring now to the drawings where like elements are designated by like reference numerals, FIGS. 1-7 illustrate a human joint 99 undergoing joint reconstruction according to an embodiment of the present invention. FIGS. 8-10 illustrate a fixation system 100 of the invention which, as described below, is inserted into a drilled hole through the joint bones using a single suture strand to obtain the repair structure of FIG. 7.

For simplicity, and according to exemplary embodiments only, the invention will be described below with reference to a particular embodiment, wherein the joint 99 is an acromioclavicular (AC) joint 99 of the human shoulder comprising clavicle 10 and coracoid 20 and undergoing acromioclavicular (AC) joint reconstruction according to an embodiment of the present invention. Also for simplicity, reference to the fixation system 100 of FIGS. 8-10 will be made in this application as to the acromioclavicular reconstruction or fixation system 100 (which is inserted into a drilled hole through the clavicle and the coracoid using a single suture strand to obtain the repair structure of FIG. 7). However, the invention is not limited to this particular acromioclavicular (AC) joint fixation system, but contemplates reconstruction and/or fixation systems for any structures (bone, cartilage, soft tissue, etc.) that need to be stabilized, fixated and/or reconstructed.

As illustrated in FIG. 8, the fixation system 100 of the present invention comprises two buttons 101, 102 joined by a continuous loop of suture 110. The buttons may have various configurations and dimensions and may be similar to, or different from, each other. For example, the buttons may be circular, oblong, rectangular or parallelepipedal, among many other configurations. Preferably, one button is circular and the other button is oblong. In the exemplary embodiment illustrated in FIG. 8, button 101 is circular and button 102 is oblong.

Figure 9A:
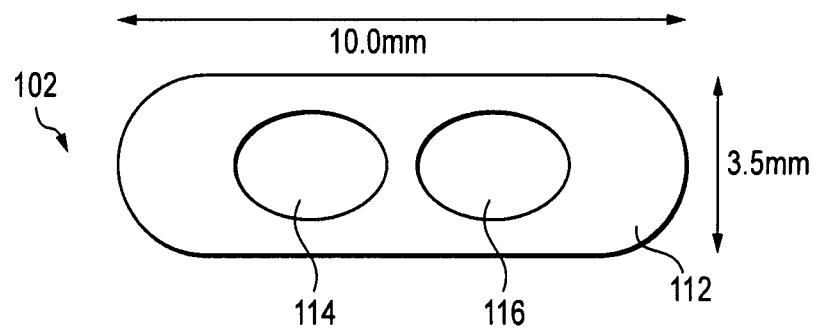
FIGS. 9a and 9b illustrate exemplary embodiments of one member of the fixation device shown in FIG. 8.
Figure 10:
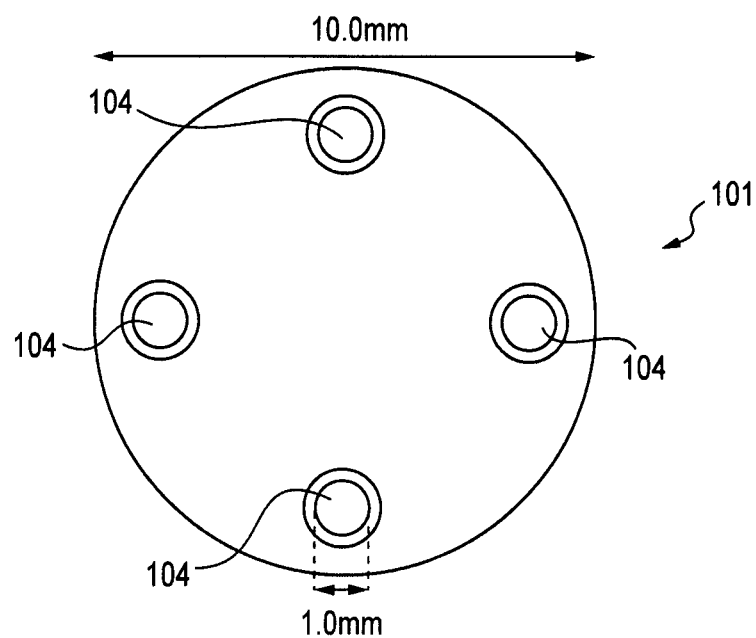
FIG. 10 illustrates an embodiment of the other member of the fixation device shown in FIG. 8.

Button 102 is illustrated in FIG. 9a as having a body 112 provided with first and second apertures 114, 116. The button 102 is preferably formed from titanium or stainless steel, although any other suitable material could be used, in particular any suitable bioabsorbable material. In the embodiment shown in FIG. 9a, the first aperture 114 and the second aperture 116 are oblong in shape, the longitudinal mid-line of each of the first and second apertures 114, 116 being located substantially about a longitudinal mid-line of the button 102. Preferably, the button 102 has a length of about 9 mm to about 20 mm, more preferably of about 12 mm to about 15 mm, and a width that is less than about 1 mm narrower than the width of the drill holes through which the button is inserted and subsequently passed through. Preferably, button 102 is very small having a width that allows it to pass through a 3 mm cortical pin hole without over drilling, which in turn saves time and preserves bone.

Figure 9B:
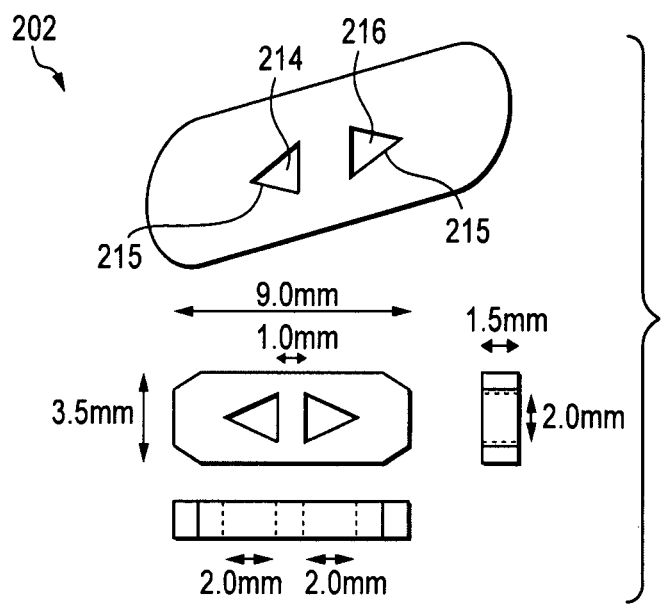

FIG. 9b illustrates yet another embodiment of a button of the present invention, indicated as 202. In the illustrated alternative embodiment, the button 202 is about 9.0 mm in length by about 3.5 mm in width, with a thickness of about 1.5 mm. The button 202 has first and second apertures 214 and 216, respectively, provided within body 212. In the illustrated alternative embodiment, each of the apertures 214, 216 are triangular in shape, the respective apices 215 being directed away from each other and being located substantially about a longitudinal mid-line of the button 202. Button 202 may be formed, for example, of metals such as titanium, titanium alloys or stainless steel, PEEK or PLLA, or other biocompatible and/or bioabsorbable materials known in the art.

FIG. 10 illustrates button 101 of the system 100 having a circular or disc-shaped configuration. The button 101 is preferably formed from titanium or stainless steel although, as known to those skilled in the art, any other suitable material, in particular any suitable bioabsorbable materials, may be used. The button 101 also has at least two flexible coupling-locating apertures 104. In the illustrated embodiment, there are four apertures 104 circumferentially arranged about the outer edge of the button. In the illustrated embodiment only, each of the apertures 104 has a diameter of about 1.0 mm. Each of the apertures 104 may have beveled edges, above and below, or only above, or only below.

Flexible strand or continuous loop 110 extends between at least one of the apertures of the first button 101 and at least one of the apertures of the second button 102. Flexible strand or continuous loop 110 may be formed of suture, for example a high strength suture material such as FIBERWIRE® suture, sold by Arthrex, Inc. of Naples, Fla., and described in U.S. Pat. No. 6,716,234, the disclosure of which is incorporated by reference herein. The high strength suture may be available in various lengths and, preferably, is a #5 FIBERWIRE® suture strand. FIBERWIRE® suture is formed of an advanced, high-strength fiber material, namely ultrahigh molecular weight polyethylene (UHMWPE), sold under the tradenames SPECTRA (Honeywell) and DYNEEMA (DSM), braided with at least one other fiber, natural or synthetic, to form lengths of suture material. The suture may optionally include filaments of various colors. The suture may be also formed of a plurality of suture strands configured to separate from a single strand to a plurality of strands in the continuous loop.

Various steps of methods of acromioclavicular joint reconstruction according to embodiments of the present invention are provided below, first with reference to specific steps, and second with reference to steps relative to the structures illustrated in FIGS. 1-7.

Prior to undergoing acromioclavicular joint reconstruction, the patient is positioned in the beach chair or lateral decubitus position under a general anesthesia. Subsequently, the following actions may be undertaken: induce the arthroscope into the glenohumeral joint via a standard posterior portal; create an anterior/superior portal with an outside/in technique using a spinal needle for position; insert a 7 mm Partially Threaded Cannula into this portal; create an anterior/inferior portal near the tip of the coracoid, with an outside/in technique using the spinal needle to ensure that the base of the coracoid can be reached; insert an 8.25 mm Twist-In Cannula through this portal and start the debridement of the rotator interval; and introduce a 4.5 mm full radius shaver blade through the anterior/inferior cannula and into the rotator interval and debride until the tip of the coracoid can be visualized.

The following actions may be also performed: using a 70° arthroscope, release the middle glenohumeral ligament and partially release the middle glenohumeral ligament; retract the anterior/inferior cannula behind the rotator interval to completely reach the superior and middle glenohumeral ligaments; once the interval has been cleared, start to expose the base of the coracoid using a mechanical shaver and radiofrequency device; move the arthroscope to the superior portal to facilitate the view of the base of the coracoid; and strip the bursa and periosteum from the base of the coracoid, to obtain a full view of the undersurface.

Particular exemplary steps of the reconstruction technique of the present invention will be explained below with reference to FIGS. 1-7:

Reference is now made to FIG. 1. Insert assembled Adapteur Drill Guide C-Ring with the Coracoid Drill Stop and Graduated Guide Pin Sleeve 88 (FIG. 8) through the anterior/inferior portal. Position the drill stop tip under base 21 of the coracoid 20, as close to the scapula as possible. Position the top of the Guide Pin Sleeve over the superior clavicle 10 at its midline approximately 25 mm from the distal clavicle through a 1.5 cm incision made in Langers lines by splitting the deltotrapezial fascia.

Using a power drill, insert a drill guide pin 51 (for example, a 2.4 mm Drill Tip Guide Pin) into the guide pin sleeve and advance it through the clavicle 10 and coracoid 20. The tip of the guide pin is captured by the drill stop at the base of the coracoid under direct visualization. Check the position of the pin 51 in relation to the coracoid and, if incorrect, redrill the guide pin. Remove the C-Ring and leave the guide pin 51 in situ.

Figure 2:
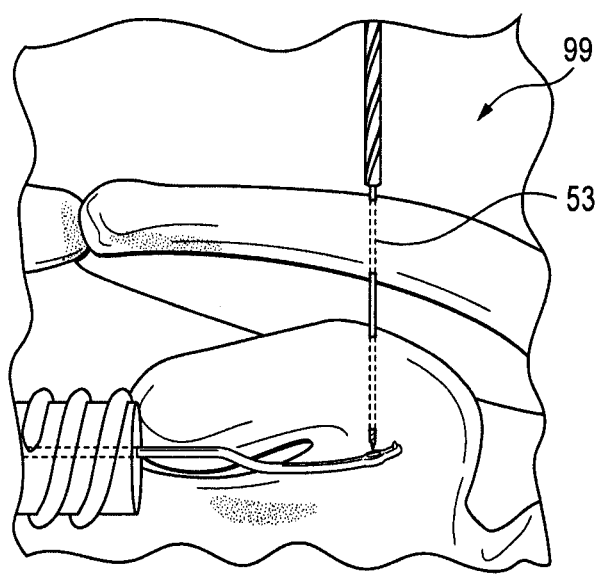
Figure 4:
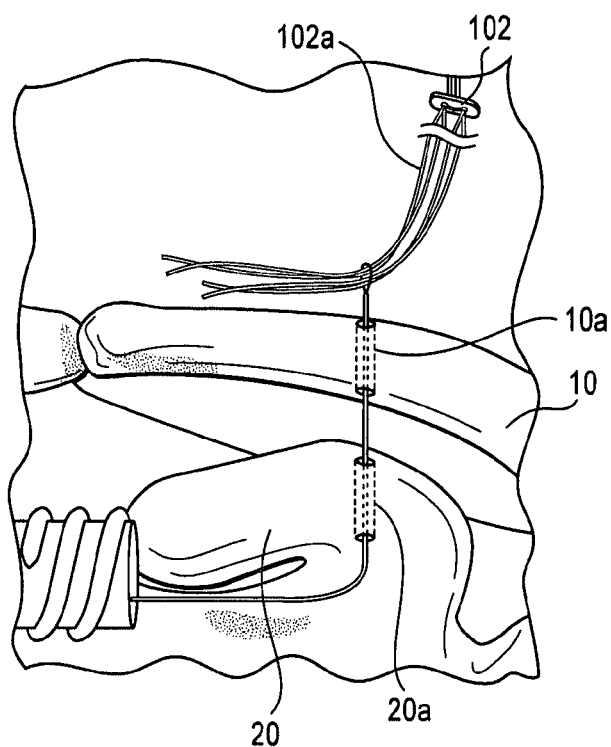

Reference is now made to FIG. 2. Attach the Coracoid Drill Stop to a handle (for example, a Tear Drop handle), to hold the guide pin 51 in place while drilling over it. Using a power drill, advance a drill 53 (for example, a 4 mm Cannulated Drill) over the pin 51 and through the clavicle and coracoid to form two passages (tunnels or holes) 10a, 20a (FIG. 4). Cannulated drilling beyond the coracoid 20 should be avoided under direct arthroscopic visualization. Remove the guide pin 51 and leave the Cannulated Drill 53 in situ.

Figure 3:
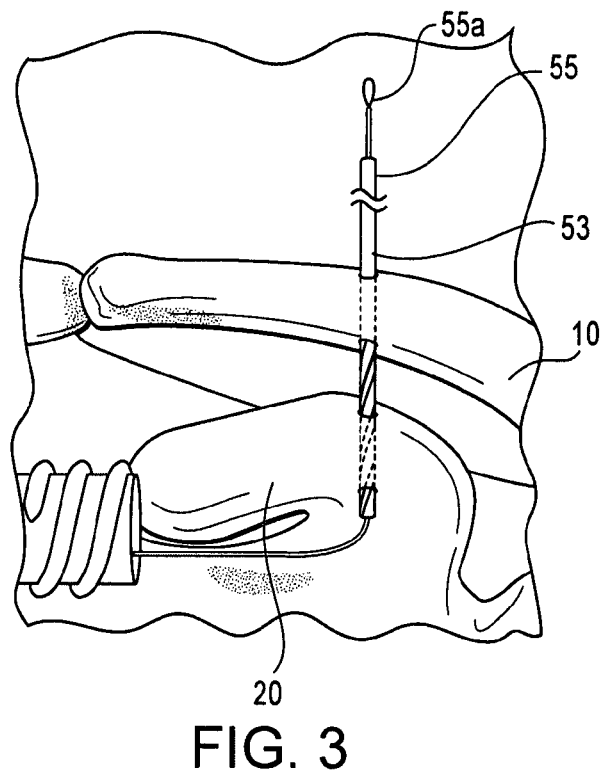

With reference to FIG. 3, advance a passing wire 55 (for example, a Nitinol suture passing wire) down through the Cannulated Drill 53 and grasp the tip with the arthroscopic grasper. Remove the drill 53 prior to delivering the wire tip out of the anterior/inferior portal, leaving wire loop 55a superiorly.

Referring to FIG. 4, insert at least one traction suture 102a (for example, two white traction sutures) from the oblong button 102 of the reconstruction system 100 (FIG. 8) through the wire loop 55a of the Nitinol suture passing wire 55.

Figure 5:
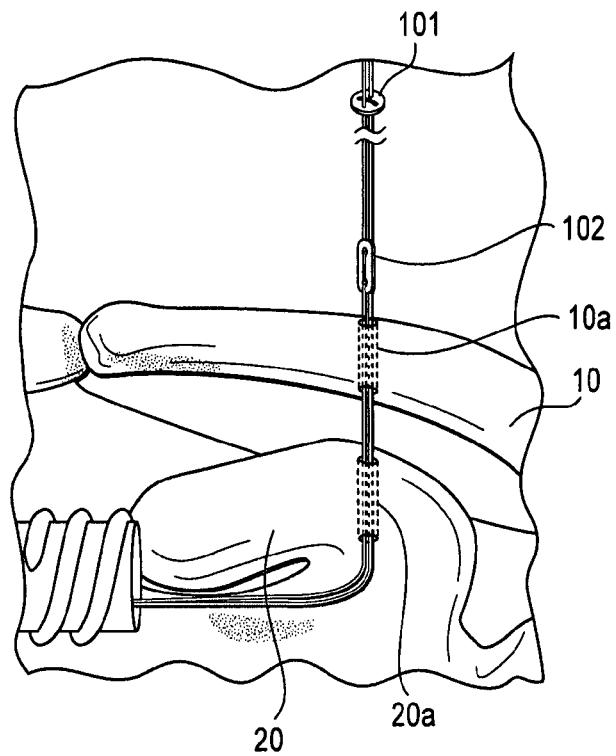

Reference is now made to FIG. 5. Pull the suture passing wire 55 to retrieve the two white traction sutures 102a out of the anterior/inferior cannula. Pull on one of the two white traction sutures 102a to flip the oblong button 102 into a vertical position suitable for advancement through the bone tunnels 10a, 20a.

Figure 6:
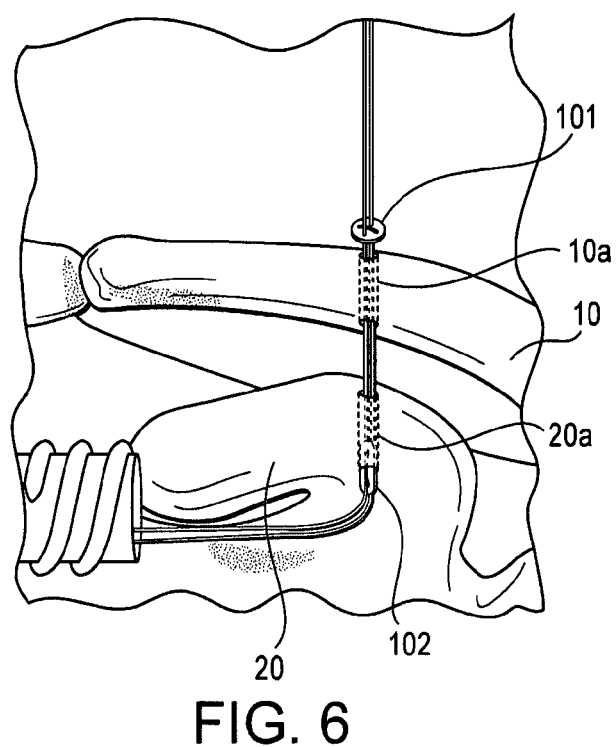

Referring to FIG. 6, advance the oblong button 102 through the bone tunnels 10a, 20a in the clavicle 10 and the coracoid 20 under direct visualization, until it exits the coracoid base 21. Independently pull on each of the white traction sutures 102a of the oblong button 102, to flip the button 102 onto the underside of the coracoid base 21.

Figure 7:
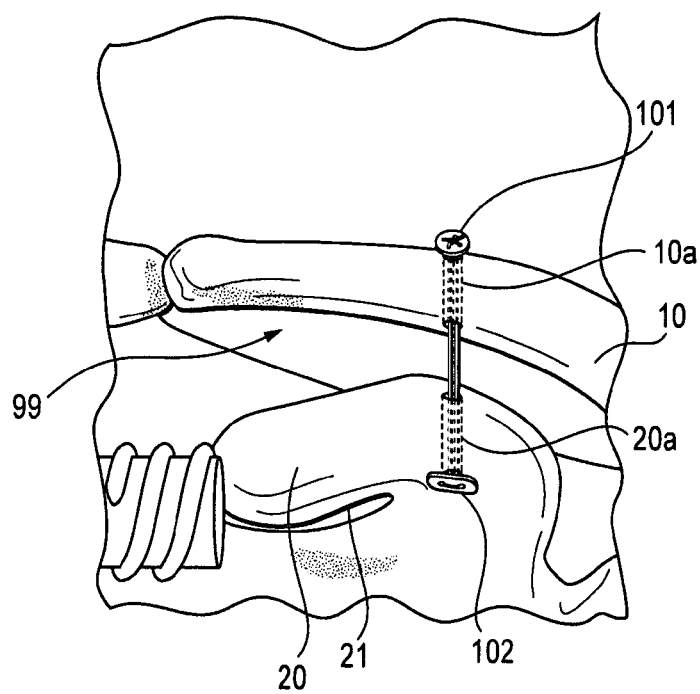
Figure 8:
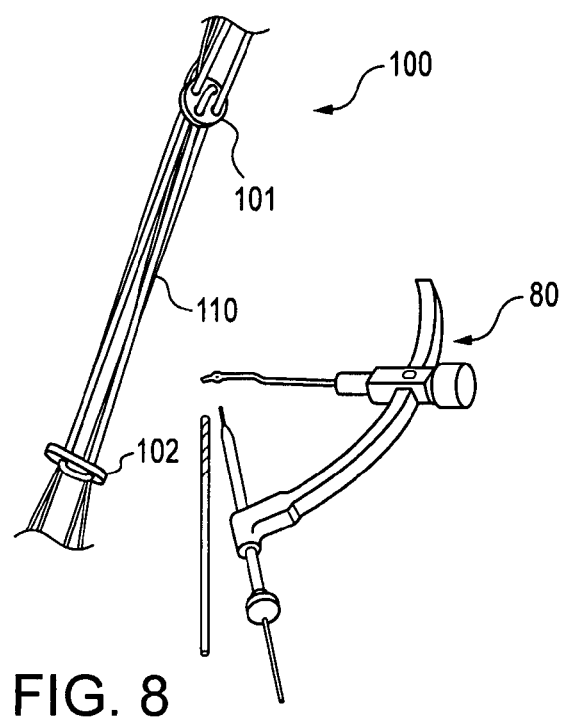
FIG. 8 is a schematic illustration of a fixation and reconstruction device of the present invention.

Once the security of the oblong button 102 is confirmed, place the arthroscope into the subacromial bursa through the posterior portal (FIG. 7). Reduce the clavicle 10 until the position is felt to be satisfactory under direct visualization. Pull on suture tails 101a (for example, two blue suture tails) of the round button 101, to advance the round button 101 down to the surface of the clavicle 10. Tie the sutures over the top of the fixation system 100 (TightRope) making, for example, a surgeon's knot and two reverse half-hitches. This step completes the reduction and stabilization of the acromioclavicular joint 99. The suture tails can be sewn under the deltotrapezial fascia to minimize the knot stack. Remove any remaining white traction sutures by cutting and putting them out of the buttons. Fluoroscopy may be used at this stage to confirm reduction.

Although the above embodiments have been described with reference to an acromioclavicular joint reconstruction, the invention is not limited to this embodiment. Accordingly, the present invention also contemplates other kinds of joint and ligament reconstructions, the acromioclavicular joint reconstruction being just illustrative.

Although the present invention has been described in relation to particular embodiments thereof, many other variations and modifications and other uses will become apparent to those skilled in the art. Accordingly, it is not intended that the present invention be limited to the illustrated embodiments, but only by the appended claims.

What is claimed as new and desired to be protected by Letters Patent of the United States is:

1. A joint fixation system, comprising:
    a circular button assembled prior to installation in a joint to an oblong button by a continuous looped flexible member having free ends, said circular button having a first body with a first shape having a first minor dimension and provided with four apertures extending through the first minor dimension and said oblong button having a second body with a second shape having a second minor dimension and provided with at least one second aperture extending through the second minor dimension, the free ends of said continuous looped flexible member extend through said minor dimension and from an exposed major dimension of said circular button;
    wherein the continuous looped flexible member is looped once through the circular button and looped twice through the oblong button, such that the free ends which extend through the circular button are capable of tractable pulling, and the continuous looped flexible member extends between the circular and oblong buttons four times and passes through all four apertures of the circular button; and
    wherein the joint fixation system compresses a first body joint tissue toward a second body joint tissue between the circular button and the oblong button when the free ends are pulled.

2. The fixation system of claim 1, wherein the continuous looped flexible member is suture.

3. The fixation system of claim 1, wherein the continuous looped flexible member comprises a braided suture.

4. The fixation system of claim 1, wherein the fixation system is an acromioclavicular joint dislocation fixation system of the shoulder.

5. A button/suture construct, comprising:
    a circular button with four apertures assembled with a continuous suture strand to an oblong button with apertures, said continuous suture strand includes more than two suture strand segments and multiple loop sections, the strand segments extend between and join the circular and oblong buttons, the suture strand is double looped through the circular and oblong buttons such that one loop section is held within the circular button and other loop sections are held within the oblong button;
    wherein the circular button, oblong button, and continuous suture strand are assembled prior to installation; and
    wherein the circular button and the oblong button are configured to be placed on opposite sides of body tissue to compress body tissue between the circular and oblong buttons.

6. The button/suture construct of claim 5, wherein the circular button and the oblong button are adapted for engagement in or on the clavicle and the coracoid, respectively.

7. The button/suture construct of claim 5, wherein at least one of the circular and oblong buttons has a length of about 9 to about 20 mm.

8. The button/suture construct of claim 5, wherein at least one of the circular and oblong buttons has a width of about 2 to about 3 mm.

9. The button/suture construct of claim 5, wherein at least one of the circular and oblong buttons is formed of a metal or a metal alloy.

10. The button/suture construct of claim 5, wherein at least one of the circular button and the oblong button is formed of a material selected from the group consisting of metals, metal alloys, PEEK and PLLA.

11. The button/suture construct of claim 5, further comprising a pull-through suture, wherein the pull-through suture is configured to pull one of the circular and oblong buttons though a tunnel formed in body tissue from a first end of the tunnel to a second end of the tunnel.

12. The button/suture construct of claim 5, wherein the suture strand has a suture portion provided between the circular button and the oblong button.

13. The button/suture construct of claim 12, wherein the suture portion has a length which is about equal to a length of an acromioclavicular joint.

* * * * *